United States Patent [19]

Whitney et al.

[11] 4,342,311

[45] Aug. 3, 1982

[54] INJECTOR WITH PROGRAMMING MEANS

[76] Inventors: Douglass G. Whitney, 2518 W. Wesley Rd.; John K. Martin, III, 2837 Ridge Wood Cir., both of Atlanta, Ga. 30327

[21] Appl. No.: 248,483

[22] Filed: Mar. 27, 1981

Related U.S. Application Data

[60] Division of Ser. No. 1,091, Jan. 8, 1979, Pat. No. 4,273,112, which is a continuation-in-part of Ser. No. 741,528, Nov. 12, 1976, Pat. No. 4,150,672, and Ser. No. 964,953, Nov. 30, 1978, Pat. No. 4,235,235.

[51] Int. Cl.³ .............................................. A61M 5/20
[52] U.S. Cl. .............................. 128/214 F; 128/218 A
[58] Field of Search ............... 128/214 F, 214 E, 215, 128/216, 213, 218 A, 253, 260; 222/63, 70, 77

[56] References Cited

U.S. PATENT DOCUMENTS

| | | | |
|---|---|---|---|
| 2,602,446 | 7/1952 | Glass et al. | 128/214 F |
| 3,880,138 | 4/1975 | Wooten et al. | 128/214 F |
| 3,964,482 | 6/1976 | Gerstel et al. | 128/214 F |
| 4,024,864 | 5/1977 | Davies et al. | 128/214 F |

Primary Examiner—John D. Yasko
Attorney, Agent, or Firm—B. J. Powell

[57] ABSTRACT

Method and apparatus for injecting fluids into patients at a controlled rate from an ampule containing the injecting fluid with a sliding piston therein to force the fluid from the ampule into the patient using a drive system which incrementally and successively advances the piston in the ampule to meter the fluid into the patient.

4 Claims, 23 Drawing Figures

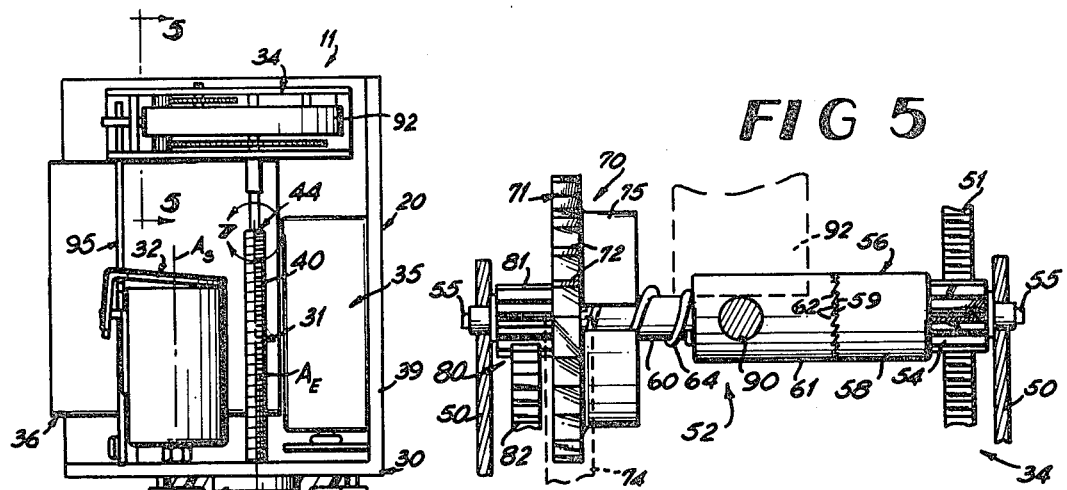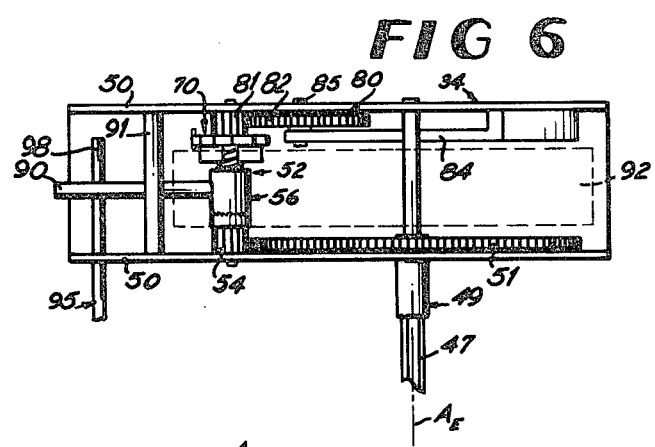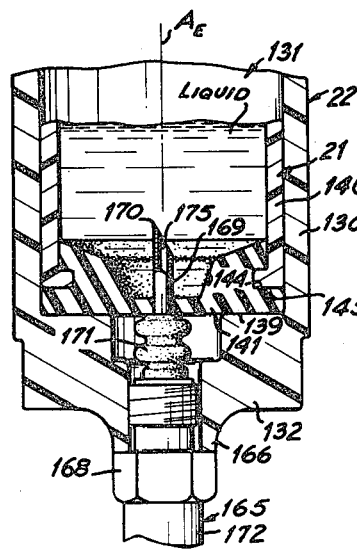

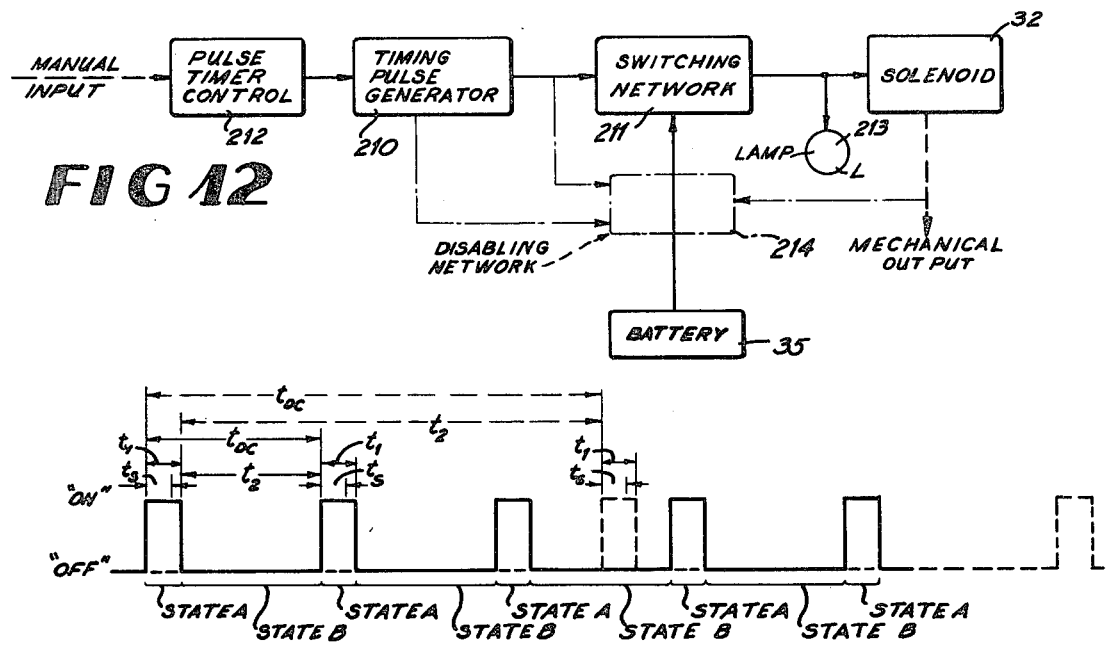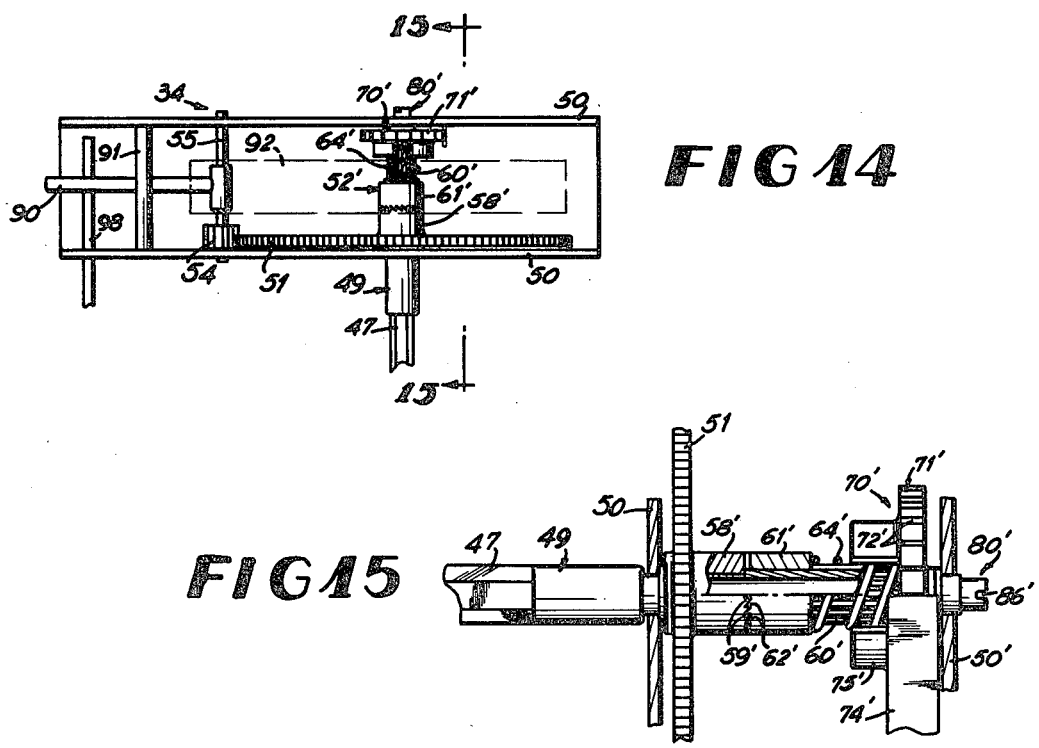

INJECTOR WITH PROGRAMMING MEANS

CROSS REFERENCE TO RELATED APPLICATIONS

This application is a division of our co-pending application Ser. No. 1,091 filed Jan. 8, 1979, now U.S. Pat. No. 4,273,112 which is a continuation-in-part of our earlier co-pending applications Ser. No. 741,528 filed Nov. 12, 1976, now U.S. Pat. No. 4,150,672, and Ser. No. 964,953 filed Nov. 30, 1978, now U.S. Pat. No. 4,235,235.

I. TECHNICAL FIELD

This invention relates generally to devices for dispensing or injecting a fluid at a controlled rate and more particularly to a device for use in the medical field to inject fluids into the body of a patient at a slow rate over a prolonged period of time.

II. BACKGROUND ART

It is desirable in the medical profession to inject fluids such as liquid medicaments into the body of the patient, whether human or animal, at a relatively slow rate over a prolonged period of time. Several varieties of medical treatments such as chemotherapy, pre- and post-surgery treatments for the prevention of blood clotting, various nutrient treatments, various antibiotic treatments and treatment of certain other diseases generally require low rates of injection over a long period of time. Such injections are generally made intravenously or subcutaneously into the patient. Some of these treatments generally require that the fluid be introduced relatively continuously over an extended period of time at varying rates ranging from very slow rates, usually about 1 cc per 24-hour period, to relatively fast rates of more than about 5 cc per 24-hour period. Because a significant increase in the predetermined rate of injection during these continuous treatments must be accurately controlled to prevent serious injury to or fatality of the patient, the rate of injection must be frequently and closely monitored.

There are a number of liquid dispensing or injection devices presently known which attempt to dispense or inject a liquid into a patient at a very slow continuous rate over an extended period of time. These prior art injection systems, however, suffer from a number of drawbacks.

One problem frequently encountered with such prior art injection systems is that the system cannot reliably inject small quantities of fluid over a prolonged period of time. To compensate for this inadequacy, medical personnel have had to dilute the liquid medicament with neutral fluids to reduce the unit liquid medicament concentration of the fluid being injected so that a relatively large quantity of fluid could be injected without overdosing the patient with the active liquid medicament and so that the undesired consequences due to variations in fluid injection rate were minimized. This, of course, increases the weight of the fluid being injected and also increases the power required to inject this larger quantity of fluid into the patient. The net result is that the overall weight of these systems due to the weight of the fluid to be injected and the weight of the necessary power supply is at a level that virtually precluded these injection systems being made sufficiently portable for the patient to carry on his usual daily activities.

Another problem commonly found with the prior art injection systems is that a failure in some component of the system can cause the injection system to exceed the desired injection rate. This not only has resulted in the use of the diluted liquid medicament but has also required frequent monitoring of the injection system by medical personnel to compensate for this problem. To further compensate for this problem, the patient has usually been confined to a medical facility so that counteractive treatment is quickly available in the event of overdosage of the patient.

III. SUMMARY OF THE INVENTION

According to the invention, there is provided a method of injecting fluid into a patient at an average prescribed injection rate over a prolonged period of time from a chamber carrying the fluid with an outlet connecting the fluid to the patient and with a piston in the chamber movable toward the outlet to force the fluid into the patient characterized by the steps of connecting the piston to a driving means constructed and arranged to move the piston only a prescribed distance toward the outlet each time the driving means is operated regardless of the length of time the driving means is operated to force a known volume of the fluid into the patient each time the piston is moved the prescribed distance at an injection rate greater than the desired average prescribed rate where the known volume is much less than the total volume of fluid to be injected over the prolonged period of time; and alternately operating and stopping the operation of the driving means to cause the fluid to be injected at the average prescribed rate over the sum of the times the driving means is operated and not operated so that, in the event of a malfunction which continuously operates the driving means, the piston will be moved only the prescribed distance toward the outlet to prevent overdosing the patient.

The method of the invention may be further characterized by operating the driving means for a fixed period of time each time the driving means is operated and stopping the operation of the driving means for a selectively variable period of time so that the average prescribed injection rate can be changed. The method of the invention may likewise be further characterized by selectively varying the prescribed distance the piston is moved each time the driving means is operated so as to vary the known volume of fluid injected each time the driving means is operated while maintaining the period of time the driving means is not operating constant to selectively change the average prescribed injection rate.

The invention also includes the apparatus for carrying out the above methods of injecting fluid into the patient. The driving means may include a solenoid, a stepping motor, or a piezoelectric device with an appropriate control means.

In summary, the invention of this application overcomes the problems and disadvantages associated with the prior art by providing an injection system which has the capability of injecting fluid slowly and precisely into a patient at a known, easily measurable and easily variable rate. The system is extremely fail-safe in that failure of any part of the device will result in disabling the device to prevent a too rapid injection rate or any further injection of the fluid. Further, the system provides a human receptive indication, visible and/or audible, of whether the device is working which can be easily and readily monitored by the patient and/or medical personnel thereby greatly reducing the number and skill of medical personnel necessary to monitor the injection rate. Because the system of the invention is able to precisely control the injection of the fluid, the volume and thus the weight of the fluid injected is minimized because of its concentrated form rather than diluted form. Also, the power required to dispense this minimized volume of fluid is minimized to minimize the power pack weight. As a result, the system of the invention can be made highly portable so that the patient is not hampered in his ambulatory capability thereby maximizing the amount of productive time available to the patient even during treatment. Because of these features, the system of the invention is ideally suited for out-patient use not presently clinically available to prevent unnecessary hospitalization and expense.

These and other features and advantages of the invention disclosed herein become more apparent upon consideration of the following detailed description and accompanying drawings wherein like characters of reference designate corresponding parts throughout the several views and in which:

BRIEF DESCRIPTION OF THE DRAWINGS

FIG. 4 is an elevational view partly shown in cross-section of that embodiment of the apparatus seen in FIG. 3;

FIG. 5 is an enlarged view of the ratchet mechanism of the apparatus taken along line 5—5 in FIG. 4;

FIG. 6 is enlarged view of the transmission in FIG. 4;

FIG. 7 is an enlarged view of that portion encircled by line 7 in FIG. 4 and shown partly in cross-section;

FIG. 8 is an enlarged view of that portion encircled by line 8 in FIG. 4 and shown partly in cross-section;

FIG. 12 is an electrical block diagram of the controller circuit of the invention seen in FIGS. 1–3;

FIG. 13 is a graphic illustration of the control circuit of FIG. 12;

FIG. 14 is a view similar to FIG. 6 illustrating a modification of the invention;

FIG. 15 is an enlarged side view taken along line 15—15 in FIG. 14;

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Figure 1:
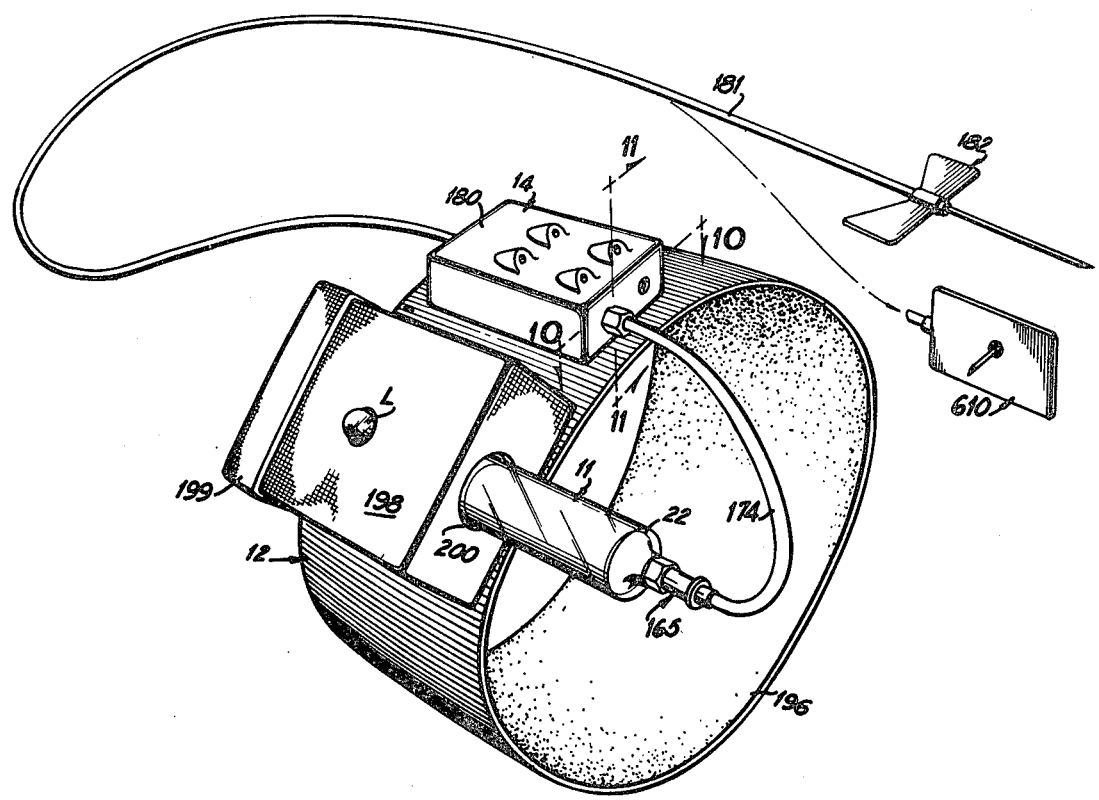
FIG. 1 is a perspective view illustrating the invention.
Figure 2:
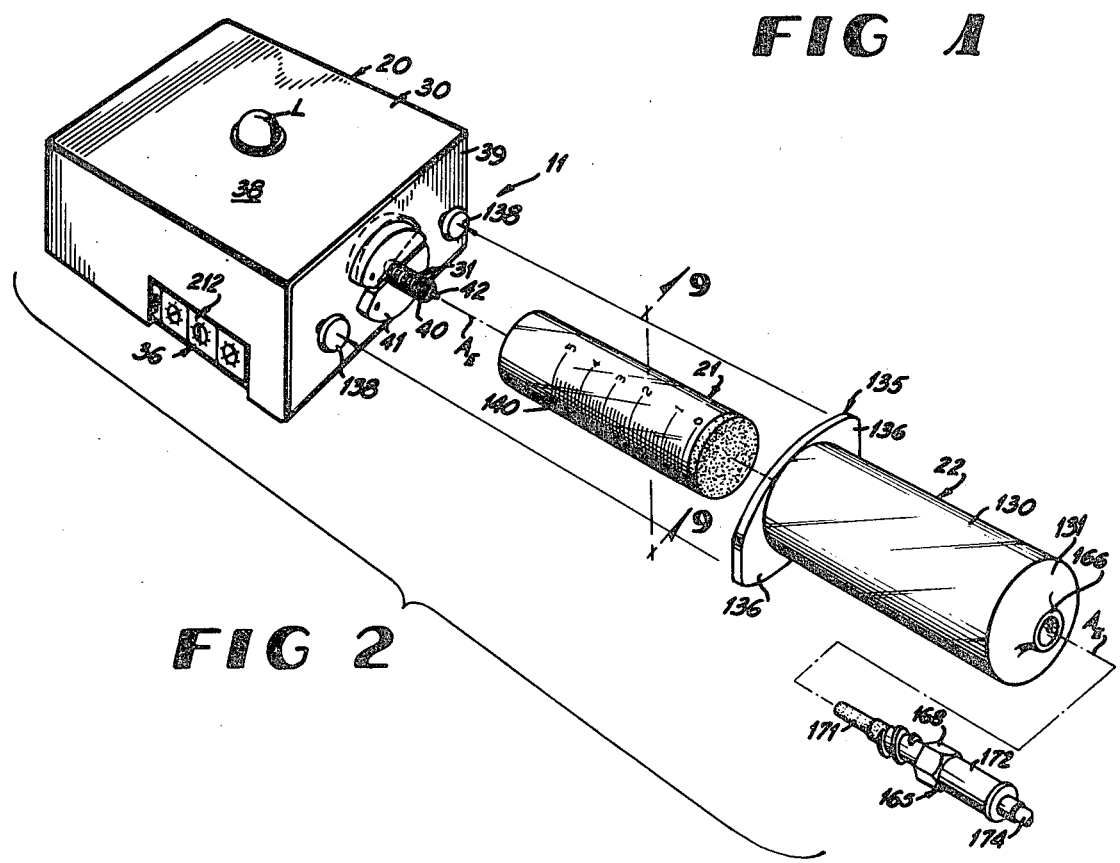
FIG. 2 is an exploded perspective view illustrating the injection apparatus of the invention.

Referring to FIG. 1, it will be seen that the fluid injection system 10 includes an injector 11, a carrier 12 for mounting the injector on the patient, and a connector assembly 14 for connecting the output of injector 10 to the patient, usually intravenously or subcutaneously. FIG. 2 illustrates the injector 11 in more detail. The injector 11 has a power unit 20 for selectively forcing a fluid from the ampule or container 21 carrying the fluid. The ampule 21 is positioned on the power unit 20 by an ampule holder 22. Thus, the fluid from the ampule 21 is forced into the patient by the power unit 20 via the connector assembly 14.

Figure 3:
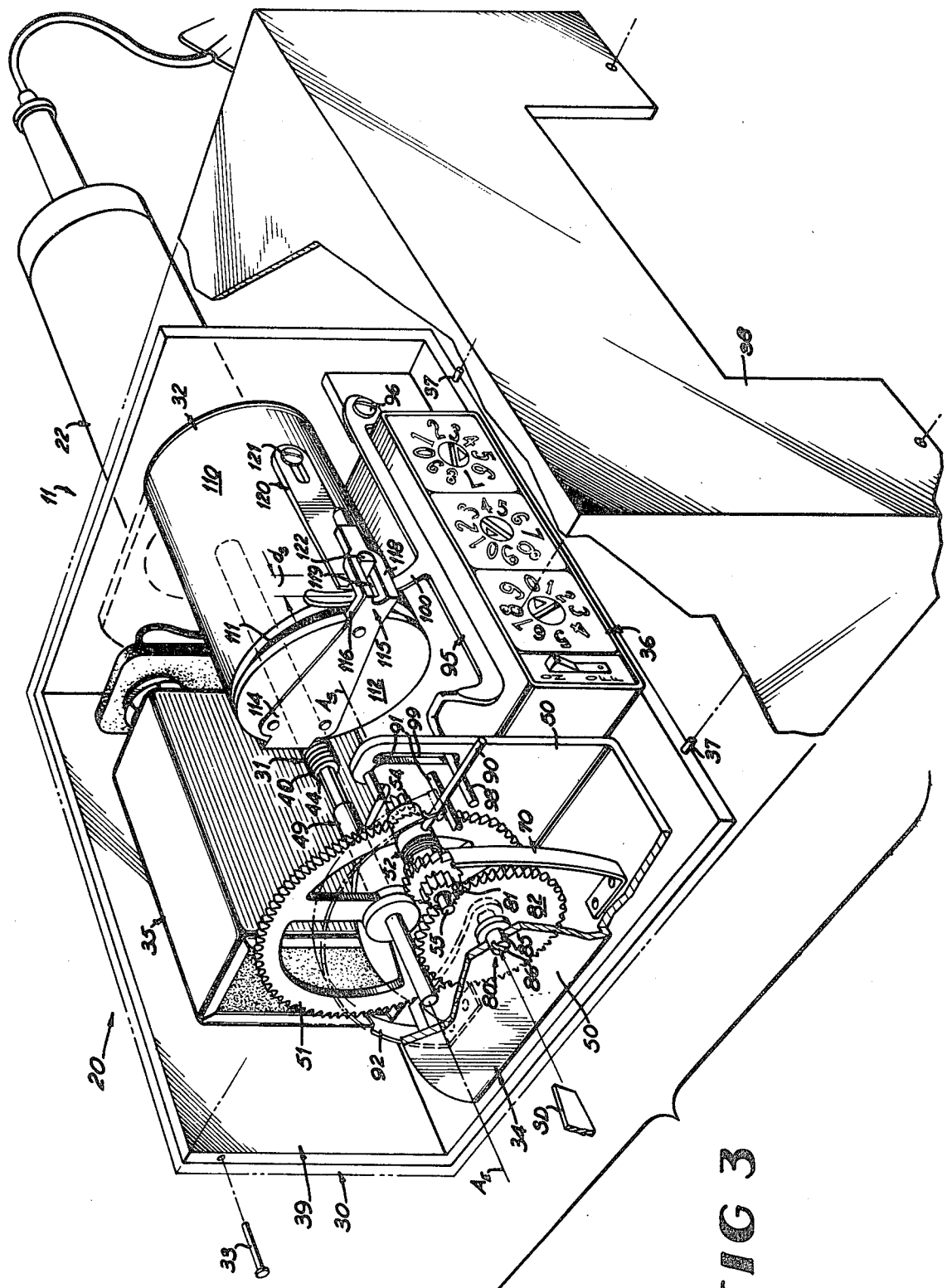
FIG. 3 is an enlarged exploded perspective view illustrating a first embodiment of the apparatus seen in FIG. 2 with portions thereof broken away to show the construction thereof.

A first embodiment of the power unit 20 is seen in FIGS. 2–5. The power unit 20 includes a housing 30 which removably mounts the ampule holder 22 thereon about an expelling axis $A_E$ (FIG. 2) as will become more apparent. The housing 30 mounts a drive screw assembly 31 therein about the expelling axis $A_E$ to expel fluid from the ampule 21 carried in holder 22 as will become more apparent. The drive screw assembly 31 is driven by a driving solenoid 32 through a transmission 34 (FIG. 3). A battery 35 is provided to power solenoid 32 through a controller 36.

The housing 30 has a base 39 which mounts the various components thereon. A removable cover 38 is adapted to fit over base 39 to enclose the components mounted on the base. Locating pins 37 maintain cover 38 in alignment with base 39 and latch pin 33 keeps cover 38 in place as best seen in FIG. 3.

The drive screw assembly 31 includes an externally threaded drive screw 40 (FIGS. 2–4) which forces the fluid from ampule 21. The drive screw 40 is positioned coaxially along the expelling axis $A_E$ by an internally threaded split nut 41 (FIGS. 2 and 4) mounted on the base 39 of housing 30 so that nut 41 is axially fixed along axis $A_E$. Nut 41 can be opened as seen by dashed lines in FIG. 2 to release the drive screw 40 so that it can be manually moved axially along axis $A_E$ and nut 41 reengaged as will become more apparent. With nut 41 closed to engage drive screw 40, rotation of drive screw 40 shifts drive screw 40 axially along the expelling axis $A_E$. The outboard end of drive screw 40 projecting outside of housing 30 is provided with a pointed driving projection 42 (FIGS. 2 and 9) which engages the piston in the ampule 21 as will become more apparent.

Figure 9:
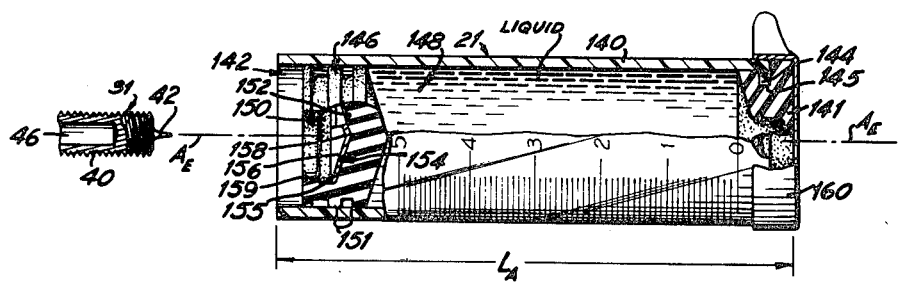
FIG. 9 is an enlarged view taken along line 9—9 in FIG. 2 showing the ampule.

The drive screw 40 is driven through a slip joint 44 (FIGS. 3, 4 and 7). The slip joint 44 is provided through a driven member 45 (FIG. 7) affixed to the inboard end of the drive screw 40. The drive screw 40 defines an axially extending passage 46 therein opening onto its inboard end with the passage 46 being closed by driven member 45. The driven member 45 defines a noncircular driven passage 48 therethrough which is shown as being hexagonal in shape. The driven passage 48 is centered on the expelling axis $A_E$. A drive shaft 49 with a driving section 47 having a cross-sectional shape complementary to the driven passage 48 in driven member 45 slidably extends therethrough so that rotation of drive shaft 49 rotates the drive screw 40. The driving section 47 on drive shaft 49 projecting through the driven member 45 is freely received in the passage 46 in drive screw 40. The passage 46 extends along the length of drive screw 40 terminating just inboard of the projecting end of the drive screw 40 as seen in FIG. 9 so that clearance for the driving section 47 on drive shaft 49 is provided when drive screw 40 is fully retracted into housing 30.

The drive shaft 49 is rotatably journalled in bearings mounted in support plates 50 of the transmission 34 as seen in FIG. 6 so that the central axis of the drive shaft 49 is coaxial with the expelling axis $A_E$. The journalled connections between the drive shaft 49 and the support plates 50 prevent axial movement of the drive shaft 49 along the expelling axis $A_E$ while allowing the drive shaft 49 to be rotated about the expelling axis $A_E$. Thus, it will be seen that, as the drive shaft 49 is rotated clockwise as seen in FIG. 3 with the nut 41 closed about the drive screw 40, the drive screw 40 will be rotated to axially displace the drive screw 40 along the expelling axis $A_E$ and move the pointed driving projection 42 on the projecting end of the drive screw 40 out of the housing 30.

To retract the drive screw 40 back into the housing 30, the split nut 41 is opened as shown by dashed lines in FIG. 2 and the drive screw 40 manually pushed back into the housing 30 with the driving section 47 on the drive shaft 49 sliding through the driven member 45. After the drive screw 40 has been retracted back into the housing 30, the split nut 41 is reclosed to reengage the drive screw 40 so that it can be driven back out of the housing 30 by rotating the drive shaft 49.

The transmission 34 (FIGS. 3-6) is powered by solenoid 32 to rotate the drive shaft 49. The drive shaft 49 serves as the output of the transmission 34 with an output spur gear 51 fixedly mounted on the drive shaft 49 between the support plates 50 so that rotation of the output spur gear 51 rotates the drive shaft 49. The output spur gear 51 is rotatably driven by an input ratchet assembly 52 driven by the driving solenoid 32.

The input ratchet assembly 52 (FIGS. 3 and 5) includes a spur drive pinion 54 mounted on a pinion shaft 55 rotatably journalled between the support plates 50. The pinion shaft 55 also mounts thereon a ratchet mechanism 56 which includes a driven ratchet member 58 defining ratchet teeth 59 thereon about a positioning boss 60. The driven ratchet member 58 is fixed to the pinion shaft 55 so that rotation of the driven ratchet member 58 also rotates the pinion shaft 55 and thus the spur drive pinion 54. Driving ratchet member 61 is rotatably mounted about the positioning boss 60 for both rotational movement about the boss 60 and axial movement along the boss 60. The driving ratchet member 61 includes ratchet teeth 62 thereon which are complementary to the ratchet teeth 59 on the driven ratchet member 58. The ratchet teeth 62 face the ratchet teeth 59 so that, when the driven ratchet member 61 is forced toward the ratchet teeth 59 on the driven ratchet member 58, the ratchet teeth 62 on the driving ratchet member 61 engage the ratchet teeth 59 on the driven ratchet member 58 whereby rotation of driving ratchet member 61 counterclockwise as seen in FIG. 3 rotates the driven ratchet member 58 therewith thus rotating the spur drive pinion 54. When the driving ratchet member 61 is rotated clockwise as seen in FIG. 3, the ratchet teeth 62 can slip over the ratchet teeth 59 so that the driven ratchet member 58 can be held stationary while the driving ratchet member 61 rotates with respect thereto. A ratchet spring 64 is positioned around the positioning boss 60 on that side of the driving ratchet member 61 opposite the ratchet teeth 59 on driven ratchet member 58 so that the ratchet spring 64 constantly forces the driving ratchet member 61 toward the teeth 59 on the driven ratchet member 58 to maintain the ratchet teeth 59 and 60 in driving engagement with each other, yet the ratchet teeth 62 on the driving ratchet member 61 can ratchet over the ratchet teeth 59 on the driven ratchet member 58 when the driving ratchet member 61 is moved clockwise as seen in FIG. 3.

A ratchet clutch assembly 70 (FIGS. 3 and 5) is provided in the input ratchet assembly 52 to prevent the driven ratchet member 58 from being rotated in a clockwise direction as seen in FIG. 3. The ratchet clutch assembly 70 includes a ratchet wheel 71 affixed to the pinion shaft 55 and provided with peripheral ratchet teeth 72 which are engaged by a resilient stop member 74 best seen in FIG. 3. The ratchet teeth 72 on the ratchet wheel 71 are oriented with respect to the resilient stop member 74 so that the ratchet wheel 71 can rotate with the pinion shaft 55 in a counterclockwise direction as seen in FIG. 3; however, the resilient stop member 74 engages the ratchet teeth 72 when an attempt is made to rotate the pinion shaft 55 in the clockwise direction to prevent the ratchet wheel 71 and thus the pinion shaft 55 from being rotated in a clockwise direction. This serves to prevent the driven ratchet member 58 and thus the spur drive pinion 54 from being rotated in a clockwise direction as seen in FIG. 3. Because the stop member 74 is resilient, it will be deflected over the ratchet teeth 72 as the pinion shaft 55 and ratchet wheel 71 are rotated in the counterclockwise direction. The ratchet wheel 71 also serves to captivate the ratchet spring 64 between it and the driving ratchet member 61 so that the driving ratchet member 61 is forced toward the ratchet teeth 59 on the driven ratchet member 58. The ratchet wheel 71 is provided with locating flange 75 thereon which extends over the ratchet spring 64 to prevent inadvertent dislodgement of the ratchet spring 64.

The transmission 34 is also provided with a manually operated flush mechanism 80 (FIGS. 3, 5 and 6) which drives the output spur gear 51 through the input ratchet assembly 52 to allow the drive screw 40 to be manually rotated for flushing the injector as will become more apparent. The manually operated flush mechanism 80 includes a driven spur pinion 81 affixed to the pinion shaft 55 adjacent the ratchet wheel 71 opposite the ratchet mechanism 56. The driven spur pinion 81 meshes with a manually driven spur gear 82 journalled between one of the support plates 50 on the transmission 34 and a subplate 84 as best seen in FIGS. 3 and 6. The shaft 85 carrying the spur gear 82 extends through the support plate 50 and is provided with a drive slot 86 in the projecting end thereof outside of the support plate 50 so that the drive slot 86 can be engaged through an appropriate opening by a manually operated tool such as a screwdriver SD partly seen in FIG. 3 to rotate the shaft 85 and spur gear 82. This rotates the driven spur pinion 81 to drive the pinion shaft 55. It will also be noted that the ratchet clutch assembly 70 permits the pinion shaft 55 only to be rotated in the counterclockwise direction as seen in FIG. 3. Thus, the shaft 85 carrying the spur gear 82 can be rotated only in the clockwise direction to extend drive screw 40. Because of the gear ratio of the spur gear 82 with respect to the spur pinion 81, the drive screw 40 can be relatively rapidly extended to flush the injector 11 as will become more apparent.

Alternatively, a flush mechanism may be provided by extending the projecting end of the drive shaft 49 through that support plate 50 most remote from its driving section 47 and making a slot similar to slot 86 in shaft 85 in the projecting end of drive shaft 49 to be engaged similarly to shaft 85 to manually rotate shaft 49 clockwise. This would eliminate the flush mechanism 80 while still providing a flushing capability. The input ratchet assembly 52 and ratchet clutch assembly 70 would permit flushing in the same manner as explained for flush mechanism 80.

The driving ratchet member 61 is provided with a driving projecting 90 (FIGS. 3, 5 and 6) which is used to rotate the driving ratchet member 61. The movement of the driving projection 90 rotating the driving ratchet member 61 is limited by upper and lower stops 91 extending above and below the driving projection 90 between the support plates 50 as seen in FIG. 3. The driving projection 90 is constantly urged in a clockwise direction toward the lower stop 91 as seen in FIG. 3 by a leaf spring 92 as will become more apparent.

The driving projection 90 is pivoted in counterclockwise direction as seen in FIG. 3 by a drive arm 95 pivoted on the base 39 of housing 30 at 96. The drive arm 95 has a projecting end 98 which extends through a slot 99 in one of the support plates 50 to engage the driving projection 90 in opposition to the leaf spring 92. The drive arm 95 also has a driving projection 100 thereon which is engaged by a driving solenoid 32 to pivot the drive arm 95 clockwise as seen in FIG. 3 when the driving solenoid 32 is energized. This causes the projecting end 98 on the drive arm 95 to pivot the driving projection 90 counterclockwise as seen in FIG. 3 to rotate the driving ratchet member 61 counterclockwise thereby driving the drive pinion 54 counterclockwise and the output gear 51 clockwise to rotate the drive screw 40 clockwise as seen in FIG. 3 and incrementally move the pointed driving projection 42 on the end of the drive screw 40 out of the housing 30. When the driving solenoid 32 is de-energized, the leaf spring 92 pivots the driving projection 90 clockwise as seen in FIG. 3 while pivoting the drive arm 95 counterclockwise as seen in FIG. 3 to reset the drive for another advancement of the drive screw 40.

The driving solenoid 32 is mounted on the base 39 as best seen in FIG. 3 about an axis $A_S$. The solenoid 32 has an open ended tubular cylindrical case 110 which mounts an actuator coil 111 therein. A circular actuator plate 112 is pivoted to one end of the case 110 by a hinge spring member 114 so that the actuator plate 112 is magnetically responsive to the actuator coil 11. The actuator plate 112 is seen in its deactivated or open position in FIG. 3. Activation of the actuator coil 111 pivots the actuator plate 112 toward the open end of the cylindrical case 110 to its activated or closed position. The movement of the actuator plate 112 is stopped by the end of case 110. The actuator plate 112 has an L-shaped driving projection 115 thereon with a driving section 116 coplanar with the actuator plate 112 and a check section 118 which extends along the side of the case 110 generally parallel to the solenoid axis $A_S$. The check section 118 is provided with a check slot 119 therein which is engaged by a check member 120 adjustably mounted on the case 110 by a locking screw 121. The check member 120 has a check projection 122 which extends through the check slot 119 in the driving projection 115 to limit the amount of movement of the driving projection 115 as the actuator plate 112 moves away from the open end of case 110 to its deactivated position. The actuator plate 112 is constantly urged toward its deactivated position by the resiliency of hinge spring member 114 as well as the leaf spring 92 in the transmission 34.

Since the movement of the actuator plate 112 toward the open end of case 110 when coil 111 is energized is arrested by the end of case 110 and since the movement of the actuator plate 112 away from the open end of case 110 when coil 11 is de-energized is arrested by the check projection 122, the amount of movement of the driving section 116 on the driving projection 115 can thus be adjusted with the locking screw 121 holding the check member 120 on the case 110. Thus, the driving section 116 on the driving projection 115 is moved the adjustable distance $d_S$ seen in FIG. 3 as the actuator plate 112 is moved from its deactuated position to its actuated position. The arcuate driving projection 100 on the drive arm 95 extends behind the driving section 116 on the driving projection 115 as seen in FIG. 3 so that the closure of actuator plate 112 when coil 110 is energized serves to pivot the drive arm 95 clockwise as seen in FIG. 3. This in turn causes the projecting end 98 on the drive arm 95 to pivot the driving projection 90 connected to the driving ratchet member 61 to rotate the drive pinion 54 counterclockwise and the drive shaft 49 clockwise through output spur gear 51 to screw the drive screw 40 in the split nut 41 and move the pointed driving projection 42 out of the housing 30 as will become more apparent.

It will also be appreciated that the input ratchet assembly and the ratchet clutch assembly may be used to connect the output spur gear 51 to the drive shaft 49 rather than connecting pinion shaft 55 to input drive pinion 54. This is illustrated in FIGS. 14 and 15. FIG. 14 corresponds generally to FIG. 6 and FIG. 15 is taken along line 15—15 in FIG. 14 to show the connection between the output spur gear 51 and drive shaft 49. The input ratchet assembly has been designated 52' and the check clutch assembly has been designated 70' in FIGS. 14 and 15.

From FIG. 14, it will be seen that the driving projection 90 is connected directly to the pinion shaft 55 and input drive pinion 54. The pivoting movement of projection 90 is still limited by the stops 91, driven in a counterclockwise direction by the driving projection 98 on drive arm 95, and urged in a clockwise direction by the leaf spring 92 in the manner described above.

As seen in FIG. 15, however, the output spur gear 51 is rotatably journalled about the drive shaft 49 rather than being affixed thereto so that gear 51 is free to rotate about shaft 49. The input ratchet assembly 52' serves to connect gear 51 to drive shaft 49 so that rotation of gear 51 clockwise, when viewed in the same direction as that seen in FIG. 3, will rotate shaft 49 but allows gear 51 to rotate in the opposite direction without rotating drive shaft 49 as will become more apparent.

Driving ratchet member 58' is affixed to the spur gear 51 so that it rotates therewith. An internally splined driven ratchet member 61' is mounted on the drive shaft 49 between support plates 50 via an externally splined connector 60' affixed to shaft 49. Connector 60' permits driven ratchet member 61' to slide axially along shaft 49 but rotation of driven ratchet member 61' positively rotates the drive shaft 49. The ends of ratchet members 58' and 61' facing each other are respectively provided with meshing ratchet teeth 59' and 62'. Teeth 59' and 62' are constructed so that the driving ratchet teeth 59' rotate the driven ratchet member 61' and drive shaft 49 through driven ratchet teeth 62' when spur gear 51 is rotated clockwise when viewed as in FIG. 3; however, the driving teeth 59' can slip over teeth 62' when gear 51 is rotated counterclockwise so that drive shaft 49 will not be rotated counterclockwise. Ratchet spring 64' urges teeth 59' and 62' together to maintain them in mesh.

The ratchet clutch assembly 70' (FIG. 15) is provided in the input ratchet assembly 52' to prevent the drive ratchet member 61' and thus drive shaft 49 from being rotated in a counterclockwise direction when viewed in FIG. 3. The ratchet clutch assembly 70' includes ratchet wheel 71' affixed to the drive shaft 49 and is provided with peripheral ratchet teeth 72' which are engaged by a resilient stop member 74'. The ratchet teeth 72' on the ratchet wheel 71' are oriented with respect to the resilient stop member 74' so that the ratchet wheel 71' can rotate with the drive shaft 49 in a clockwise direction when viewed as in FIG. 3; however, the resilient stop member 74' engages the ratchet teeth 72' when an attempt is made to rotate the drive shaft 49 in the counterclockwise direction to prevent the ratchet wheel 71' and thus the drive shaft 49 from being rotated in a counterclockwise direction. Because the stop member 74' is resilient, it will be deflected over the ratchet teeth 72' as the drive shaft 49 and ratchet wheel 71' are rotated in the clockwise direction. The ratchet wheel 71' also serves to captivate the ratchet spring 64 between it and the driven ratchet member 61' so that the driven ratchet member 61' is forced toward the ratchet teeth 59' on the driving ratchet member 58'. The ratchet wheel 71' may be provided with locating flange 75' to prevent inadvertent dislodgement of the ratchet spring 64'.

The flushing function is provided by flush mechanism 80' best seen in FIG. 15. The drive shaft 49 projects through the support plate 50 opposite the driving section 47 on shaft 49 and is provided with a driving slot 86'. Engaging slot 86' with a tool such as the screwdriver mentioned for use with slot 86 in flush mechanism 80 permits the drive shaft 49 to be directly rotated clockwise as viewed in FIG. 3. The driven ratchet member 61' can ratchet over ratchet member 59' so that gear 51 need not be rotated. The ratchet clutch mechanism 70' prevents rotation of shaft 49 counterclockwise.

The ampule holder 22 serves to locate the fluid ampule 21 coaxially about the expelling axis $A_E$ best seen in FIGS. 2, 4 and 8 with the ampule 21 operatively associated with the pointed driving projection 42 on the drive screw 40 as will become more apparent. The ampule holder 22 has a tubular side wall 130 defining an ampule receiving chamber 131 therein closed at its outboard end by end wall 132 and open at its inboard end. The chamber 131 is sized so that the ampule 21 will just slidably fit in chamber 131 as will become more apparent. The holder 22 is removably attached to housing 30 by a bayonet type connector 135. Blades 136 of connector 135 are mounted on the side wall 130 of holder 22 adjacent its inboard end which cooperate with spaced apart locking pins 138 on the base 39 of housing 30 on diametrically opposite sides of the split nut 41 to lock the holder 22 on housing 30 with the holder coaxial with the expelling axis $A_E$.

The holder 22 also serves to maintain the split nut 41 closed about drive screw 40 as seen in FIG. 4 to insure positive threaded engagement between screw 40 and nut 41. The inside diameter of the side wall 130 is substantially equal to the outside diameter of nut 41 in its closed position so that, when the inboard end of side wall 130 is placed around nut 41, it is positively held closed and maintained in its closed position until the ampule holder 22 is removed.

The ampule 21 is illustrated in FIGS. 2, 4, 8 and 9 and serves to carry the liquid medicament which is to be injected into the patient. Ampule 21 has a tubular side wall 140 with central passage 142 closed at its outboard end by a penetrable rubber plug 141 and open at its inboard end. The side wall 140 is of constant outside and inside diameter with an outside diameter such that it is just slidably received in chamber 131 in holder 22. The length $L_A$ of ampule 21 is such that ampule 21 just fits in chamber 131 between the annular arresting shoulder 139 (FIG. 8) in holder 22 adjacent its outboard end the split nut 41 when holder 22 is locked in position as seen in FIG. 4.

The side wall 140 of ampule 21 has an inwardly directed lip 144 at its outboard end seen in FIG. 9 that engages an annular groove 145 around plug 141 to hold it in place. A resilient expelling piston 146 is slidably received in the central passage 142 through its open inboard end and in sealing engagement with side wall 140 to form a liquid chamber 148 between piston 146 and plug 141. The liquid medicament, usually in concentrated form, fills the liquid chamber 148. When an opening is made in the rubber plug 141 as will become more apparent, the liquid medicament in the fluid chamber 148 can be expelled by moving the piston 146 toward the plug 141. Because the ampule side wall 140 is coaxial with the expelling axis $A_E$ when positioned by the holder 22, the piston 146 will also be positioned for movement coaxially along the axis $A_E$. This aligns the piston 146 with the drive screw 40 as will become more apparent.

As best seen in FIG. 9, the expelling piston 146 defines a driving cavity 150 therein facing the driving projection 42 on the projecting end of the drive screw 40. The piston 146 has annular sealing rings 151 therearound to form a sliding seal with the ampule side wall 140. The driving cavity 150 opens onto the inboard end of piston 146 with its outboard end closed by a conical, forwardly tapering driven surface 152 whose apex is centered on the expelling axis $A_E$. The surface 152 tapers uniformly about the axis $A_E$ so that the driving projection 42 on the drive screw 40 is aligned with the apex of surface 152.

A conical driving plate 154 is carried in the driving cavity 150 to transfer the motion of screw 40 to piston 146. The conical driving plate 154 has a conical, forwardly tapering driving surface 155 complementary to the driven surface 152 in cavity 150 on its outboard side so that the plate 154 bears against the driven surface 152. The conical driving plate 154 also has a like conical, forwardly tapering transfer surface 156 on its inboard side facing the driving projection 42. The transfer surface 156 is aligned with the driving surface 155 so that the apex 158 of the transfer surface 156 is in alignment with the pointed driving projection 42 on drive screw 40. Thus, the pointed projection on drive screw 40 bears against the apex 158 of transfer surface 156 to drive piston 146. The driving surface 155 on driving plate 154 insures that the piston 146 will be smoothly moved along ampule 21 without canting to expel the liquid in the chamber 148.

The driving plate 154 is maintained in cavity 150 in piston 146 by an inwardly directed annular resilient lip 159 as best seen in FIG. 9. Because the lip 159 and piston 146 are resilient, the driving plate 154 can be forced into cavity 150 past the lip. After the driving plate 154 is forced into cavity 150, the lip 159 reassumes the shape shown in FIG. 9 to keep plate 154 in place.

The volume of liquid medicament carried by ampule 21 is, of course, determined by the internal diameter of the side wall 140 as well as the length $L_A$ of the ampule. The size is usually selected so that some convenient volume of liquid medicament is carried in the liquid chamber 48. The side wall 140 of the ampule 21 is usually graduated to indicate the volume therein and is illustrated as containing about 5 cc of liquid medicament. Usually, the ampule 21 is designed to carry that volume of liquid which is to be dispensed over a 24-hour period. Because different treatments require widely different volumes, it would be desirable and within the scope of the invention that different volumes of liquid medicament be carried in the ampule 21, depending on the particular treatment requirements.

The exposed surface of the penetrable rubber plug 141 enclosing the end of the ampule may be covered by a tear-off cover member 160 as seen in FIG. 9 to insure the sterility of this surface. Because the liquid chamber 148 is completely enclosed by the rubber plug 141, the ampule side wall 140 and the piston 146, the sterility of the liquid medicament carried in the ampule is maintained prior to its being used.

The outlet through the penetrable rubber plug 141 in the end of the ampule 21 is provided by a piercing cap assembly 165 best seen in FIGS. 2 and 8 mounted in the outboard end of the ampule holder 22. The piercing cap assembly 165 is attached to a boss 166 on the outboard side of the end wall 132 on holder 22 so that the piercing cap assembly 165 is oriented coaxially with respect to the expelling axis $A_E$. The piercing cap assembly 165 includes an externally threaded mount 168 that can be screwed into the internal threads provided in the hole through the boss 166. The externally threaded mount 168 has a piercing needle 169 extending therethrough with a pointed end 170 projecting from the mount 168 into the outboard end of the ampule receiving chamber 131 along the expelling axis $A_E$. The pointed end 170 of needle 169 extends sufficiently far into the ampule receiving chamber 131 to insure that the pointed end 170 pierces the penetrable rubber plug 141 in the outboard end of the ampule 21 when the ampule 21 is pushed into place. A penetrable needle cover 171 may be provided over the pointed end 170 of needle 169 so that, when the penetrable rubber plug 141 in the outboard end of the ampule 21 is forced toward the pointed end of the piercing needle 169, the penetrable needle cover 171 will be penetrated by the pointed end 170 of the piercing needle 169 prior to the pointed end 170 piercing the penetrable rubber plug 141 in the ampule 21. This is best illustrated in FIG. 8.

An appropriate connector 172 connects the delivery tubing 174 in connector assembly 14 to the passage 175 through the piercing needle 169. Passage 175 serves as the outlet from the liquid chamber 148 of the ampule 21. Thus, it will be seen that, as the piston 146 is forced toward the penetrable rubber plug 141, the liquid medicament in the ampule 21 will be forced out through the passage 175 in the piercing needle 169 and into the delivery tubing 174.

The delivery tubing 174 may be connected directly to the patient or may be connected to the patient via connector assembly as seen in FIG. 1. The connector assembly 14 as seen in FIG. 1 includes a manifold block 180 illustrated in more detail in FIGS. 10 and 11. The manifold block 180 may be permanently or removably attached to the carrier 12. Block 180 has a common delivery tube 181 therefrom to which is connected a common intravenous injection needle assembly 182 or subcutaneous injection needle assembly 610 for connection to the patient. Both types of needles 182 and 610 are illustrated in FIG. 1. Subcutaneous injection needle assembly 610 is of the type described in our co-pending application Ser. No. 964,953.

Figure 10:
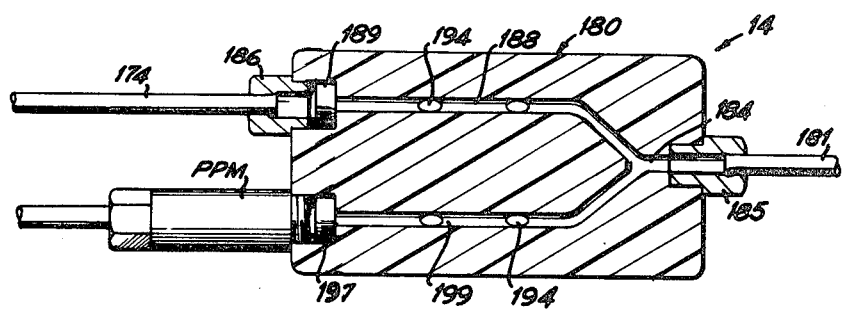
FIG. 10 is an enlarged cross-sectional view taken along line 10—10 in FIG. 1.
Figure 11:
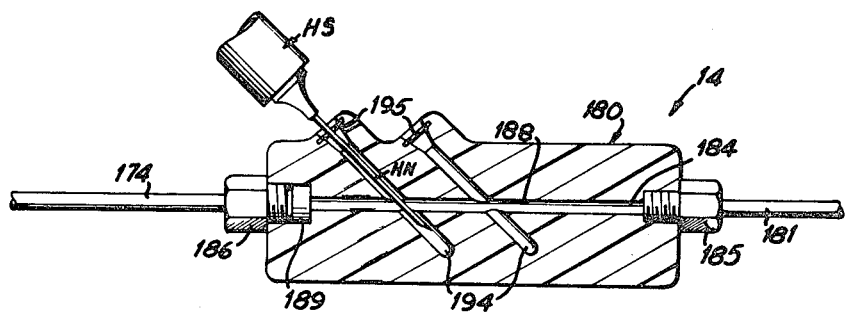
FIG. 11 is an enlarged cross-sectional view taken along line 11—11 in FIG. 1.

The common delivery tube 181 is in communication with a common delivery chamber 184 in block 180 through a quick disconnect 185 seen in FIGS. 10 and 11. The male coupling 186 on the delivery tubing 174 from the injector 11 is connected to a continuous injection transfer chamber 188 through a check valve 189. Chamber 188 is connected to the common delivery chamber 184 so that the fluid flows through the transfer chamber 188 into delivery chamber 184 and then into the patient via tube 181.

A second transfer chamber 190 may be provided in manifold block 180 to afford an additional connection point. Chamber 190 also communicates with the common delivery chamber 184 like chamber 188. The inlet to the second transfer chamber 190 is also equipped with a check valve 191 to permit liquid to only enter chamber 190 for discharge out the delivery chamber 184. Chamber 190 allows a second injector of the type shown herein or of other types to be used simultaneously with injector 11. A porous plug type metering assembly PPM from an alternate injector system is shown in FIG. 10 by way of illustration.

It is also frequently desirable to provide short injections of medication to the patient with needle devices such as the hypodermic syringe HS partly seen in FIG. 11. To accommodate these injections, the manifold block 180 is provided with cross chambers 194 best seen in FIG. 11. The cross chambers 194 intersect one of the transfer chambers 188 or 190 and each are provided with a penetrable plug 195 such as rubber so that the needle HN on the syringe HS can be inserted through plug 195 into one of the cross chambers 194. The syringe HS can then be used to inject unmetered fluid into the patient via the common delivery tube 181. Because the block 180 is made of a strong material, the needle HN will not penetrate same to prevent injection from the hypodermic syringe and also isolates the needle HS from the delivery tube 181.

The carrier 12 is designed for convenient attachment to the patient's body. It is illustrated in FIG. 1 for attachment to the patient's arm. The carrier 12 includes a wide elastic band 196 which comfortably fits over the patient's arm without significantly affecting the patient's blood circulation. A support pouch 198 is mounted thereon which defines a continuous injector pocket therein to receive the injector 11 therein. The continuous pocket is closed by a flap 199 with an appropriate mechanism to hold the flap closed. A cutout 200 is provided in pouch 198 to allow the holder 22 on injector 11 to pass therethrough. The manifold block 180 is illustrated as attached to band 196.

The controller 36 serves to alternatively connect and disconnect the battery 35 to solenoid 32 at a rate such that the desired average fluid injection rate is maintained. The controller 36 is schematically illustrated in FIG. 12. Basically, the controller 36 includes a timing pulse generator 210 whose pulse output operates a switching network 211 to cause the switching network 211 to alternatively connect the solenoid 32 to and disconnect solenoid 32 from battery 35. The pulse output rate from the timing pulse generator 210 can be manually adjusted through the pulse time control 212. The pulse timer control 212 is illustrated in FIGS. 2 and 3 as three manually adjustable potentiometers although different timer control arrangements may be used.

The pulse generator output is schematically illustrated in FIG. 13. While the output is illustrated as a square wave, it is not intended to be limiting since a variety of wave shapes may be used that functionally operate the switching network 211 in the manner described. Basically, the output from generator 210 has a duty cycle where the output goes to state A with time interval $t_1$ and then to state B with time interval $t_2$ during each duty cycle. State A causes the switching network 211 to connect the battery 35 to solenoid 32 to activate it and state B causes the switching network 211 to disconnect battery 35 from solenoid 32 to deactivate it. The physical characteristics of solenoid 32 are such that it takes a prescribed maximum time interval $t_s$ as seen in FIG. 13 after output from generator 210 goes to state A for the actuator plate 112 on solenoid 32 to move to its activated or closed position. Thus, the time interval $t_1$ that the output from generator 210 remains in state A is selected to be slightly longer than the maximum solenoid actuation time interval $t_s$ to insure full operation of actuator plate 112. On the other hand, since continued activation of solenoid 32 has no further effect on the movement of plate 112 after it reaches its activated or closed position, the time interval $t_1$ is selected to be as short as possible to conserve the energy of battery 35 and thus extend battery life. Since the solenoid 32 injects a fixed amount of liquid medicament each time it is activated and since the pulse generator output goes to state A once each duty cycle, varying the time period $t_{DC}$ (FIG. 13) of each duty cycle changes the injection rate. Because of the fixed actuation time $t_s$ of solenoid 32, the time interval $t_1$ can be maintained constant regardless of the pulse rate of the output generator 210. Thus, since about the same fixed amount of liquid medicament is expelled from ampule 21 each time solenoid 32 is activated, the overall injection rate can be controlled by varying the time interval $t_2$. This is done by adjusting the pulse timer control 212.

FIG. 13 graphically illustrates two pulse rates, a faster rate shown by solid lines and a slower rate shown by dashed lines. The time interval $t_1$ is the same for both rates while time interval $t_2$ is varied. This, of course, varies the duty cycle time period $t_{DC}$.

An indicator mechanism 23 such as lamp L seen in FIGS. 1 and 2 or an audible sound generator may be used to provide an indication that the injector is operating. The indicator mechanism may be activated when the output from generator 210 is in state A or state B. Since state A is usually shorter than state B, however, it would usually be activated in response to state A to extend battery life.

By appropriately selecting the components of controller 36, the gear ratios of the various mechanical components of power unit 20 and the size of ampule 21, the setting of the pulse time control 212 can be made to correspond to the injection rate delivered. For instance, with the three potentiometers illustrated in the control 212, the setting could correspond to the injection rate to two decimal places. As an example, the setting illustrated in FIG. 3 would correspond to an injection rate of 1.95 cc per 24-hour period. This facilitates adjustment of injection rate.

It will be appreciated that the overall gear ratio of transmission 34 and the drive screw assembly 31 will be determined by the size of the ampule 21, the stroke of the projecting end 98 of the drive arm 95 when solenoid 32 is energized, and the desired incremental volume of liquid medicament to be injected each time the solenoid 32 is energized. Simply for ease of monitoring, one set of parameters used was one energized time each minute for solenoid 32 when an injection rate of about 1 cc per 24-hour period was selected. Under these requirements and with the construction illustrated in FIGS. 1–9, an overall gear ratio of about 229:1 was satisfactory where the drive screw 40 has 32 threads per inch. Thus, each time solenoid 32 is energized, about 0.0007 cc of liquid medicament is dispensed.

Any conventional battery 35 may be used provided it has a sufficient voltage output to power controller 36 and solenoid 32. The particular battery 35 illustrated is a 9 volt transistor type alkaline battery.

To protect against the controller 36 overdosing the patient through failure of one or more of the components, the battery 35 may be connected to the switching network 211 through a disabling monitor network 214 shown by phantom lines in FIG. 12. The disabling monitor network 214 is provided with a feedback circuit from the timing pulse generator 210 and the output of the pulse generator 210 so that malfunction of the timing pulse generator 210 causes the feedback circuit to activate the disabling monitor network 214 to cause the disabling monitor network 214 to disconnect the battery 35 from the switching network 211 and thus disable the solenoid 32. A motion sensor may be operatively associated with the mechanical output of the solenoid 32 to provide another input to the disabling monitor network 214 so that, if the timing pulse generator 210 generates a signal in its output which should cause the switching network 211 to activate the solenoid 32 and no motion is sensed in the mechanical output of the solenoid 32, the disabling monitor network 214 disconnects the battery 35 from the switching network 211 to disable the solenoid 32. Thus, the disabling monitor network 214 serves to disable the solenoid 32 upon malfunction of the timing pulse generator or the failure to obtain a mechanical output from the solenoid 32 when such output should be present.

SECOND EMBODIMENT

Figure 16:
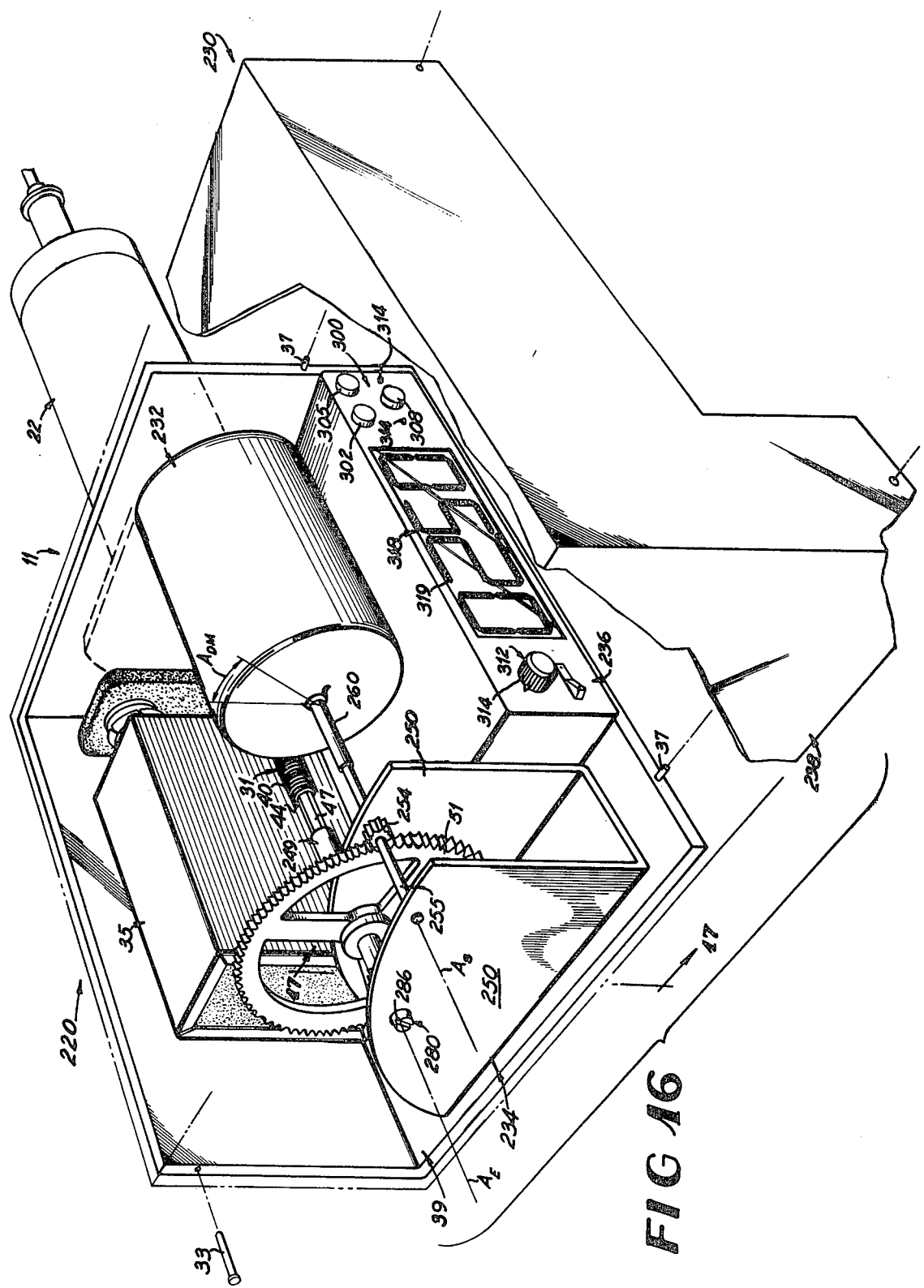
FIG. 16 is an enlarged exploded perspective view similar to FIG. 3 illustrating a second embodiment of the apparatus of the invention.
Figure 17:
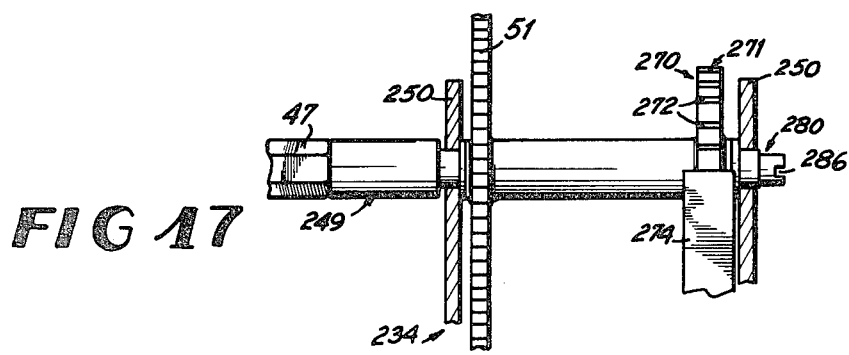
FIG. 17 is an enlarged view taken generally along line 17—17 in FIG. 16.

A second embodiment of the power unit which has been designated by the numeral 220 is seen in FIGS. 16 and 17. The power unit 220 is used in the same manner as power unit 20 for mounting the ampule 21 in the ampule holder 22 to inject fluid from the ampule into the patient via the connector assembly 14. Attention is invited to the disclosure of these components hereinabove and will not be redescribed. Those components of the power unit 220 which are common with the power unit 20 have the same reference numerals applied thereto. From FIG. 16, it will be seen that the power unit 220 includes housing 230 which removably mounts the ampule holder 22 thereon about the expelling axis $A_E$ as with the first embodiment of the power unit. The housing 230 mounts drive screw assembly 31 therein about the expelling axis $A_E$ to expel fluid from the ampule 21 carried in holder 22. The drive screw assembly 31 is driven by a drive motor 232 through transmission 234 and battery 35 is provided to power motor 232 through a controller 236.

The housing 230 has base 39 common with power unit 20 which mounts the various components thereon. A removal cover 238 is adapted to fit over base 39 to enclose components mounted on the base and has a construction the same as the cover 38 for the power unit 20 except that the cutout for the controller 236 is slightly larger in the cover 238. Like housing 30 for power unit 20, locating pins 37 maintain cover 238 in alignment with base 39, and latch pin 33 keeps cover 238 in place.

The drive screw assembly 31 includes the externally threaded drive screw 40 the same as with power unit 20 which is maintained coaxially along the expelling axis $A_E$ by the internally threaded split nut 41 (not seen in FIG. 14), the same as with the power unit 20. Thus, the drive screw 40 is axially moved along the expelling axis $A_E$ simply by rotating the drive screw 40 with respect to the split nut 41.

The drive screw assembly 231 also is driven through slip joint 44 with drive shaft 249 having a driving section 47 thereon the same as with the drive shaft 49 in the power unit 20. The drive shaft 249 is rotatably journalled in bearings mounted in the support plates 250 of transmission 234 as best seen in FIG. 16 so that the drive shaft 249 is maintained coaxial with the expelling axis $A_E$. Similarly to drive shaft 49 of the power unit 20, the journal connections between the drive shaft 249 and support plates 250 prevent axial movement of the drive shaft 249 on the expelling axis $A_E$ while allowing the drive shaft 249 to be rotated about that axis. The drive screw 40 is retracted in the same manner as the drive screw 40 in the power unit 20.

The transmission 234 is powered by the motor 232 to rotate the drive shaft 249 as will become apparent. The drive shaft 249 serves as the output of the transmission 234 with the output spur gear 51 fixedly mounted on the drive shaft 249 between the support plates 250 so that rotation of the output spur gear 51 rotates drive shaft 249 similarly to that described with the first embodiment of the power unit. The output spur gear 51 is rotatably driven by an input pinion 254 mounted on an input shaft 255 journalled between the support plates 250 of the transmission 234. The input shaft 255 is driven by the motor 232 as will become more apparent so that rotation of the input shaft 255 by motor 232 rotates the output spur gear 51 and thus the drive screw 40 to extend it.

The transmission 234 is provided with a manually operated flush mechanism 280 as seen in FIGS. 16 and 17 which allows the drive shaft 249 to be manually rotated for flushing the injector as will become more apparent. It will be seen that the drive shaft 249 rotatably extends through the support plate 250 opposite the drive screw 40 and is provided with a drive slot 286 in the projected end thereof outside the outboard support plate 250 so that the drive slot 286 can be engaged through an appropriate opening in the cover 238 by a manually operated tool such as a screw driver illustrated in FIG. 3 so that the drive shaft 249 can be manually rotated. This allows drive shaft 249 and thus drive screw 40 to be manually rotated for flushing. It will also be noted that the flush mechanism 280 can be substituted for the flush mechanism 80 in power unit 20.

To insure that the drive motor 232 must rotate the output spur gear 51 in a clockwise direction to always extend the drive screw 40, the ratchet clutch assembly 270 seen in FIG. 17 is provided on the drive shaft 249 between the support plates 250. The ratchet clutch assembly 270 includes a ratchet wheel 271 affixed to the drive shaft 249 and is provided with peripheral ratchet teeth 272 which are engaged by a resilient stop member 274. The ratchet teeth 272 on the ratchet wheel 271 are oriented with respect to the resilient stop member 274 so that the ratchet wheel 271 can rotate with the drive shaft in a clockwise direction as seen in FIG. 16; however, the resilient stop member 274 engages the ratchet teeth 272 when an attempt is made to rotate the drive shaft 249 in the counterclockwise direction to prevent the ratchet wheel 271 and thus the drive shaft 249 from being rotated in a counterclockwise direction. Because the stop member 274 is resilient, it can be deflected over the ratchet teeth 272 as the drive shaft 249 and ratchet wheel 271 are rotated in a clockwise direction. Thus, the drive shaft 249 can only be rotated in the clockwise direction both by the drive motor 232 and when it is being manually rotated through the slot 286 when flushing.

The drive motor 232 is mounted on the base 39 as best seen in FIG. 16 coaxially about the axis $A_S$ of the input shaft 255 to transmission 234. The output shaft 260 of the motor 232 is connected directly to the input shaft 255 of transmission 234 so that rotation of output shaft 260 counterclockwise as seen in FIG. 16 rotates the output spur gear 51 clockwise thus rotating the drive screw 40 in the desired clockwise direction as seen in FIG. 16. Preferably, the motor 232 is a stepping motor which rotates its output shaft 260 through a prescribed angular displacement $A_{DM}$ as seen in FIG. 16 each time the motor 232 is activated. Thus, by selecting the appropriate gear ratio between output spur gear 51 and the drive pinion 254, the amount of extension of drive screw 40 each time the drive motor 232 is stepped can be selected. The stepping motor 232 will only step through the angle $A_{DM}$ each time it is activated regardless of the length of time it remains activated. Therefore, if the controller 236 fails while keeping motor 232 activated, it will only step one increment to prevent overinjection.

Figure 18:
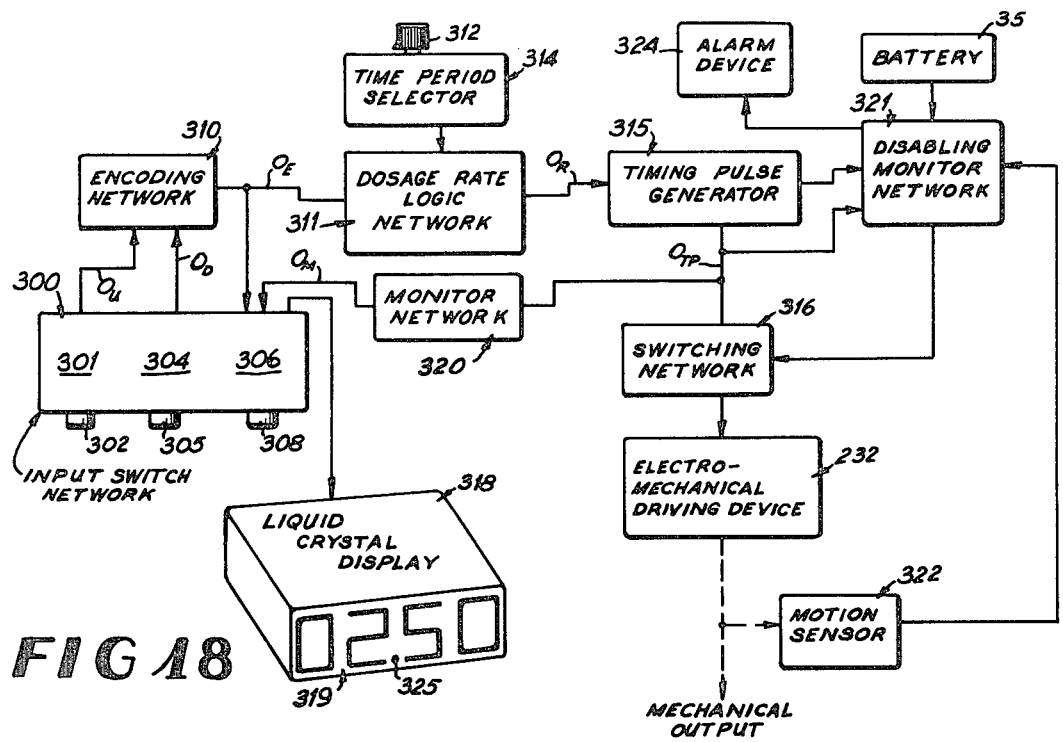
FIG. 18 is an electrical block diagram of the controller circuit of the invention seen in FIG. 16.

The controller 236 serves to alternatively connect and disconnect the battery 35 to drive motor 232 so that the liquid medicament from ampule 21 is injected into the patient at the desired rate. The controller 236 is schematically illustrated in FIG. 18. The controller 236 is selectively programmable to deliver the desired injection rate via manually operated input switch network 300. The switch network 300 includes a rate increase control switch 301 operated by rate increase input button 302, a rate decrease control switch 304 operated by rate decrease input button 305, and a mode selector switch 306 operated by actuator 308. Switches 301 and 302 respectively control outputs $O_U$ and $O_D$ to an encoding network 310 while switch 306 allows the controller 236 to be programmed while in a program mode and operate the motor 232 while in an operating mode as will become more apparent. Buttons 302 and 305 as well as actuator 308 can also be seen in FIG. 16.

The encoding network 310 generates an encoding output $O_E$ selectively adjustable through outputs $O_U$ and $O_D$ from switches 301 and 304 which is representative of the volume of liquid medicament to be dispensed over a selected time period as will become more apparent. The output $O_E$ is connected to one of the inputs of mode selector switch 306 and also to the input of a dosage rate logic network 311.

The dosage rate logic network 311 calculates the pulse rate required to dispense the selected volume of liquid medicament represented by output $O_E$ in equal increments over the manually selected time period through manual adjustment of selector actuator 312 on time period selector 314. Actuator 312 is seen in FIG. 16 also. After calculating the required pulse rate, the regulating output $O_R$ from logic network 311 adjusts the timing pulse output $O_{TP}$ of the timing pulse generator 315. Output $O_{TP}$ controls switching network 316 to connect and disconnect the motor 232 to battery 35. Because controller 236 is equally applicable to the other embodiments of the power unit, the motor is illustrated as an electro-mechanical driving device. The operation of the timing pulse generator 315 and switching network 316 may correspond to that already described for generator 210 and switching network 211.

The mode selector switch 306 has a first position which allows the controller 236 to be programmed and a second position which allows the injection rate to be monitored. In the first position, the switch 306 connects the output $O_E$ from the encoding network 310 to a liquid crystal display 318 so that the amount of liquid medicament to be dispensed is visually indicated by the liquid crystal readout 319. In the first position, selector switch 306 also enables the rate increase and decrease control switches 301 and 304 while disabling the timing pulse generator 315 to prevent injection during programming. The personnel programming the injection rate operates switches 301 and 304 to establish the desired amount of liquid medicament to be injected. Depressing input button 302 on rate increase switch 301 operates encoding network 310 to increase the displayed output $O_E$ in the liquid crystal readout 319, while depressing input button 305 on the rate decrease switch 304 operates encoding network 310 to decrease the displayed output $O_E$ in the liquid crystal readout 319.

Preferably, the encoding network 310 is constructed so that, the longer the button 302 or 305 is depressed, the faster the displayed output $O_E$ is increased or decreased as the case may be. This allows the personnel to rapidly run encoding network 310 until the displayed output $O_E$ reaches the vicinity of the desired amount to be injected, release the button 302 or 305, and then press the appropriate button 302 or 305 to finally adjust the displayed output $O_E$.

After the desired amount of liquid medicament is displayed in readout 319, the mode selector switch 306 is transferred to the operation mode via actuator 308. The particular mode of switch 306 may be indicated by indicator lights 313 seen in FIG. 16. The actuator 312 on time period selector 314 has usually already been set at the desired time period over which the amount of liquid medicament is to be injected. The time periods available may be appropriately changed. However, since the injection rates are usually based on increments of a twenty-four hour period, it will probably be convenient to have a twenty-four hour period and several other shorter periods. When the mode selector switch 306 is in the operation mode, the control switches 301 and 304 are disabled to prevent changing output $O_E$ from encoding network 310 to the dosage rate logic network 311. The dosage rate logic network 311, based on the output $O_E$ and the setting of the time period selector 314, calculates the pulse rate requirements to inject the liquid medicament into the patient and then adjusts its regulating output $O_R$ to the timing pulse generator 315 to cause the timing pulse generator 315 to generate the appropriate timing pulse output $O_{TP}$ to switching network 316 to operate motor 232 at the required stepping rate to inject the liquid medicament at the desired rate.

To provide a visual indication of the actual injection rate, a monitor network 320 is connected to the output $O_{TP}$ from the pulse generator 315 and generates a monitored output $O_M$ to the liquid crystal display 318 via mode selector switch 306 when it is in the operation mode. The monitor network 320 may also be connected to the time period selector 314 so that the monitored rate is adjusted for different time periods.

To protect against the controller 236 overdosing the patient, the battery 35 is connected to the switching network 316 through a disabling monitor network 321. The disabling monitor network 321 is provided with a feedback circuit from the timing pulse generator 315 and the output $O_{TP}$ of generator 315 so that, malfunction of the timing pulse generator 315 causes the feedback circuit to activate the disabling monitor network 321 to cause the disabling monitor network 321 to disconnect the battery 35 from the switching network 316 and thus disable the motor 232. A motion sensor 322 is operatively associated with the mechanical output of the electro-mechanical driving device to provide another input to the disabling monitor network 321 so that, if the timing pulse generator 315 generates a signal in its output $O_{TP}$ which should cause the switching network 316 to activate the electro-mechanical driving device and no motion is sensed in the mechanical output of the electro-mechanical driving device by the motion sensor 22, the disabling monitor network 321 disconnects the battery 35 from the switching network 316 to disable the electro-mechanical driving device. Thus, the disabling monitor network 321 serves to disable the electro-mechanical driving device upon malfunction of the timing pulse generator or the failure to obtain a mechanical output from the electro-mechanical driving device when such output should be present. An alarm device 324 may be provided to the disabling monitor network 321 to provide an alarm that the system is malfunctioning to warn the patient and/or the personnel who is monitoring the injection of the liquid medicament into the patient.

Figure 19:
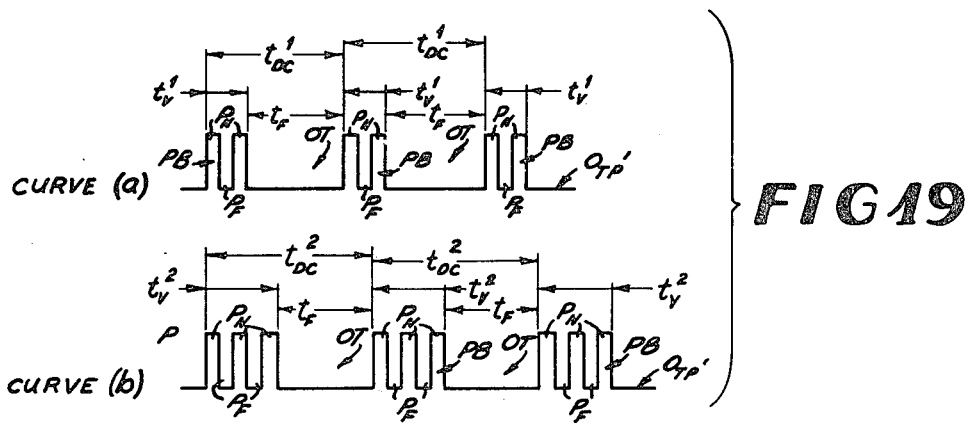
FIG. 19 is a graphic illustration of the control output of the controller circuit illustrated in FIG. 18.

It will be seen that the output $O_{TP}$ from the timing pulse generator 315 and the operation of the switching circuit 316 may be the same as that described for the first embodiment of the invention. That is, the electro-mechanical driving device may be activated for a fixed period of time and deactivated for a variable period of time to change the injection rate. Thus, one duty cycle of the timing pulse generator consists of the fixed "on" time plus the variable "off" time. On the other hand, the duty cycle of the timing pulse generator may be changed so that it has a multiple pulse duty cycle. This type of output is illustrated in FIG. 19 and has been identified as output $O_{TP}'$. Curve (a) in FIG. 19 illustrates one injection rate for the electro-mechanical driving device while Curve (b) illustrates a greater injection rate.

Output $O_{TP}'$ has an "on" pulse burst PB followed by an "off" time OT. The pulse burst PB has one or more "on" pulse $P_N$ with short "off" pulses $P_F$ therebetween so that the electro-mechanical driving device can cycle. Curve (a) illustrates output $O_{TP}'$ with two "on" pulses $P_N$ and one "off" pulse $P_F$ in pulse burst PB. Thus, it will be seen that the electro-mechanical driving device will be operated two times during the pulse burst PB and then deactivated during the "off" time OT. The injection rate, then, is determined by the duty cycle time $t_{DC}^1$ of the output $O_{TP}'$ which is the pulse burst time period $t_v^1$ plus the "off" period time $t_F$. Curve (b) illustrates output $O_{TP}'$ with three "on" pulses $P_N$ and two "off" pulses $P_F$ in pulse burst PB. Thus, it will be seen that the electro-mechanical driving device will be operated three times during the pulse burst PB and then deactivated during the "off" time OT. The injection rate, then, is determined by the duty cycle time $t_{DC}^2$ of the output $O_{TP}$ which is the pulse burst time period $t_v^2$ plus the "off" period time $t_F$ and the injection rate for Curve (b) is greater than that for Curve (a). One simply increases the injection rate by increasing the number of "on" and "off" pulses $P_N$ and $P_F$ in pulse burst PB. The off time period $t_F$ between the pulse burst PB from the timing pulse generator 315 can remain fixed. For instance, where stepping motor 232 is used, the stepping motor 232 would step only two times between each "off" time OT in the output $O_{TP}'$ shown in Curve (a) while the stepping motor 232 would step three times between each "off" time OT in the output $O_{TP}'$ shown in Curve (b) in FIG. 19.

While the liquid crystal readout 319 on the liquid crystal display 318 may be changed as is appropriate, the liquid crystal readout 319 is arranged to indicate the volume of liquid medicament to be injected over the selected time period to two decimal places with the decimal point 325 being shown in FIGS. 16 and 18 on the liquid crystal readout 319. The liquid crystal readout 319 as shown in FIGS. 16 and 18 has four integers so that up to 99.99 cc of medicament can be programmed for dispensing into the patient.

Figure 20:
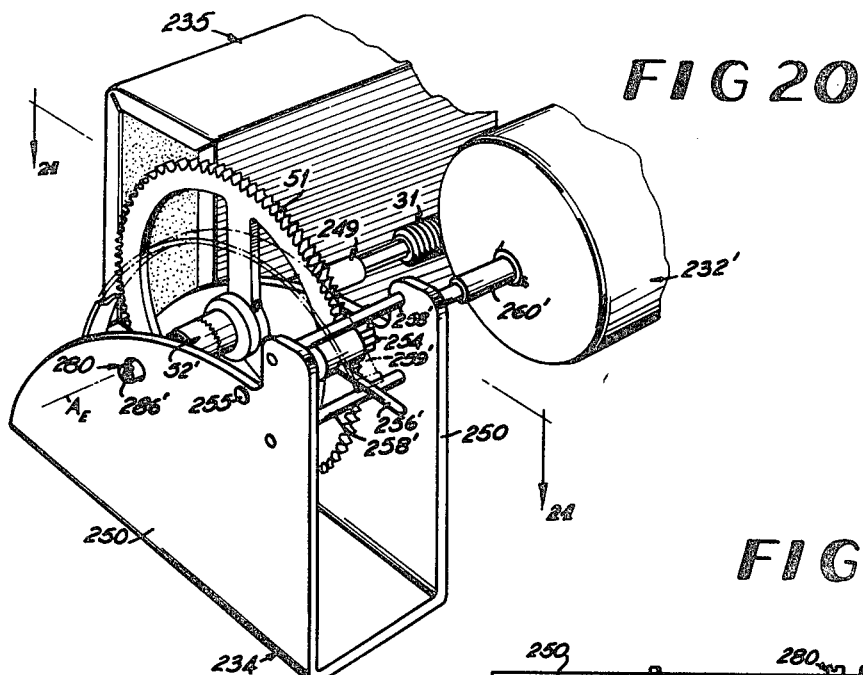
FIG. 20 is an enlarged partial perspective view illustrating a modified second embodiment of the power unit.
Figure 21:
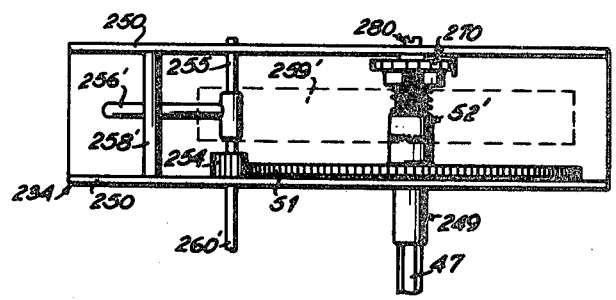
FIG. 21 is an enlarged view taken generally along line 21—21 in FIG. 20.

As seen in FIGS. 20 and 21, it will be seen that a conventional electric motor 232' may be substituted for the stepping motor 232 shown in FIGS. 16 and 17. To insure that the conventional motor 232' can only drive the output spur gear 51 a set amount, the input shaft 255 connected to the driving motor 232' may be provided with a mechanical stop projection 256' seen in FIG. 20 which extends between upper and lower stops 258' carried on support plates 250 so that the stop projection 256' can only rotate with input shaft 255 back and forth between the upper and lower stops 258'. A return spring 259' is connected between the input shaft 255 and the support plates 250 so that the input shaft 255 is constantly urged in a clockwise direction in FIG. 20. Thus, when motor 232' is not activated, the return spring 259' urges the input shaft 255 and the mechanical stop projection 256' until the stop projection 256' engages the lower stop 258' between the support plates 250. When the motor 232' is energized, it drives the input shaft 255 and the mechanical stop projection 256' in the counterclockwise direction in FIG. 20 until the stop projection 256' engages the upper stop 258' to prevent further rotation of the input shaft 255. When the drive motor 232' is de-energized, the return spring 259' rotates the input shaft 255 back to its initial position with the stop projection 256' engaging the lower stop 258'.

As best seen in FIG. 21, input ratchet assembly 52' already described is used on drive shaft 249 together with ratchet clutch assembly 270 so that the output spur gear 51 drives shaft 249 when it is rotated clockwise but can rotate back counterclockwise with input drive pinion 254 without rotating drive shaft 249. The input ratchet assembly 52' function is already described and will not be repeated here. The function of the ratchet assembly 270' has already been described and will not be repeated here. It will thus be seen that the return spring 259' rotates both the input drive pinion 254 and the output spur gear 51 back with the input shaft 255 so that the drive motor 232' always starts from the same rotational position and is able to rotate the input shaft and thus the output spur gear 51 only for a prescribed angular displacement in order that only a known fixed amount of the liquid medicament will be injected each time the drive motor 232' is energized.

Alternatively, it will also be appreciated that the conventional type drive motor 232' without the projection 256', assembly 70' and ratchet assembly 52' may be used where the amount of rotation of the drive motor 232' can be accurately controlled such as with a brake (not shown) so that, each time the controller 236 is activated, the drive motor 232' will rotate through a known angle or rotation. If such a drive motor is used, it will be appreciated that the controller 236 may be adjusted so that the pulse burst PB may be a single "on" pulse $P_N$ whose time period $t_V$ is varied.

FIRST ALTERNATE INJECTOR

Figure 22:
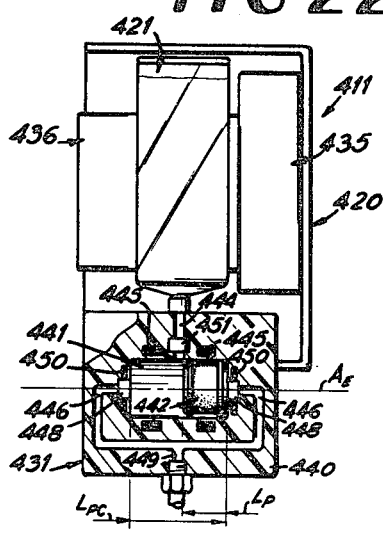
FIG. 22 is a view illustrating a first alternate embodiment of the invention.

An alternate injector which has been designated by the numeral 411 is seen in FIG. 22. The injector 41 may be mounted in the carrier 12 and connected to the connector assembly 14 for injection of liquid medicament into the patient. The injector 411 includes an expelling unit 420 and an ampule 421 which is connected to the expelling unit 420 to expel the liquid medicament carried in the ampule 421 into the patient via the connector assembly 14 (not shown in FIG. 22). The expelling unit 420 includes an expelling piston assembly 431 which is driven by a battery 435 through a controller 436. The battery 435 is the same as the battery described hereinbefore and the controller 436 corresponds to the controllers described hereinabove.

The expelling piston assembly 431 includes a housing 440 which defines an elongate cylindrical piston chamber 441 therein about an expelling axis $A_E$. The piston chamber 441 has a length $L_{PC}$ as will become more apparent. The piston chamber 441 slidably mounts a magnetically responsive piston 442 therein for sliding movement back and forth along the expelling axis $A_E$ within the piston chamber 441. It will also be noted that the magnetically responsive piston 442 is in sealing engagement with the piston chamber 441 and has a length $L_P$ which is slightly less than one-half the length $L_{PC}$ of the piston chamber 441 as will become more apparent. Thus, it will be seen that the magnetically responsive piston 442 can be slidably moved from one end of the piston chamber 441 to the other. An inlet port 444 is provided through the housing 440 into the piston chamber 441 and is centered along the length of the piston chamber 441. The length $L_P$ of the piston 442 is selected so that, when the piston 442 is in either of the opposite ends of piston chamber 441, the inlet port is in communication with that end of the piston chamber 441 in which the piston 442 is not located. Thus, it will be seen that when the piston 442 is in the end of the piston chamber 441, fluid can be introduced into the opposite end of the piston chamber 441 via the inlet port 444. A pair of solenoid coils 445 are wound around the housing 440 at opposite ends of the piston chamber 441 so that when either of the solenoid coils 445 is energized, a magnetic force will be generated which urges the magnetically responsive piston 442 toward that end of the piston chamber 441 around which the solenoid coil 445 extends. Thus, it will be seen that the piston 442 can be moved to one end of the piston chamber 441 by energizing one of the solenoid coils 445 while the piston 442 can be moved to the other end of the piston chamber 441 by energizing the other solenoid coil 445.

Each of the opposite ends of the piston chamber 441 communicates with a discharge port 446 so that, as the piston 442 moves toward each end of the piston chamber 441, any liquid between the moving piston 442 and the discharge port 446 associated with the opposite end of the piston chamber 441 will be discharged through the discharge port 446. A check valve 448 is associated with each of the discharge ports 446 so that the check valves 448 permit liquid to flow only from the piston chamber 441 out through the discharge port 446 associated therewith and not in the reverse direction. It will also be noted that the check valves 448 require sufficient pressure to open them that liquid flowing into the piston chamber 441 through the inlet port 444 will not leak out through the discharge port 446 in communication therewith until the piston 442 is forced toward the discharge port 446 to expel the liquid. The discharge ports 446 from opposite ends of the piston chamber 441 are connected to a common outlet port 449 which is connected to the connector assembly 14 (not shown) so that the liquid discharged out of the discharge ports 446 by the piston 442 will be injected into the patient.

To insure that the piston 442 is held in the ends of the piston chamber 441, permanent magnets 450 may be provided in the housing 440 at opposite ends of the piston chamber 441 so that, once the solenoid coil 445 has moved the piston into the end of the piston chamber 441, the permanent magnet 450 at that end of the piston chamber 441 keeps the piston 442 in that end of the piston chamber 441 until the solenoid coil 445 associated with the other end of the piston chamber 441 is energized to drive the piston 442 back toward the other end of the piston chamber 441.

It will also be seen that an inlet check valve 451 may be provided in the inlet port 444 to prevent fluid from being forced from within the piston chamber 441 out through inlet port 444. While the piston 442 is moving from one end of the chamber 441 to the other, it will be seen that the piston 442 covers the inlet port 444 so that liquid will not flow into the piston chamber 441.

The ampule 421 is different than the ampule 21 in that the ampule 421 is flexible so it can be prefilled with a known volume of liquid medicament to be injected into the patient. The movement of the piston 442 in the piston chamber 441 creates a partial vacuum behind the piston 442 so that, when the piston 442 uncovers the inlet port 444, liquid medicament from the ampule 421 having its outlet connected to the inlet port 444 can flow into the piston chamber 441 to be expelled when the piston 442 moves back toward that end of the piston chamber 441. It would likewise be noted that a permanent container may be provided in lieu of the ampule 441 which can be filled before the injector 411 is used.

The controller 436, as already explained, would be about the same as the controllers described hereinbefore except that the switching network associated with the controller would alternatively connect the "on" pulse output from the timing pulse generator to one of the solenoid coils 445 and then the other of the solenoid coils 445 to oscillate the piston 442 back and forth within the piston chamber 441. Like the other embodiments of the invention, it will be seen that the movement of the piston 442 in either direction within the piston chamber 441 can only inject a prescribed volume of fluid so that prevention of overdosage to the patient is insured.

SECOND ALTERNATE INJECTOR

Figure 23:
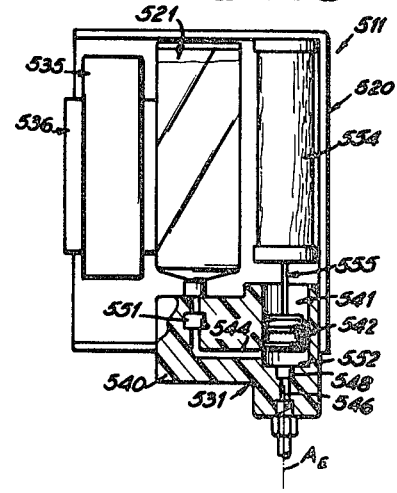
FIG. 23 is a view illustrating a second alternate embodiment of the invention.

An alternate injector which has been designated by the numeral 511 is seen in FIG. 23. The injector 511 may be mounted in the carrier 12 and connected to the connector assembly 14 for injection of liquid medicament into the patient. The injector 511 includes an expelling unit 520 and an ampule 521 which is connected to the expelling unit 520 to expel the liquid medicament carried in the ampule 521 into the patient via the connector assembly 14 (not shown in FIG. 23). The expelling unit 520 includes an expelling piston assembly 531 which is driven by a battery 535 through a controller 536. The battery 535 is the same as the battery described hereinbefore and the controller 536 corresponds to the controllers described hereinabove.

The expelling piston assembly 531 includes a housing 540 which defines a cylindrical piston chamber 541 therein about an expelling axis $A_E$. The piston chamber 541 slidably mounts an expelling piston 542 therein for sliding movement back and forth along the expelling axis $A_E$ within the piston chamber 541. Thus, it will be seen that the piston 542 can be slidably moved from its retracted position seen in FIG. 23 toward and away from the discharge end 552 of the piston chamber 541. An inlet port 544 is provided through the housing 540 into the piston chamber 541 between piston 542 and discharge end 552 of chamber 541 so that, when piston 542 is in its retracted position, the chamber 541 between piston 542 and discharge end 552 can be filled with liquid medicament via port 544.

The discharge end 552 of the piston chamber 541 communicates with a discharge port 546 so that, as the piston 542 moves toward the discharge end 552 of the piston chamber 541, liquid between the moving piston 542 and the discharge port 546 will be discharged through the discharge port 546. A check valve 548 is associated with discharge port 546 to permit liquid to flow only from the piston chamber 541 out through the discharge port 546 and not in the reverse direction. It will also be noted that the check valve 548 requires sufficient pressure to open it that liquid flowing into the piston chamber 541 through the inlet port 544 will not leak out through the discharge port 546 until piston 542 is forced toward the discharge port 546 to expel the liquid. The discharge port 546 is connected to the connector assembly 14 (not shown) so that the liquid discharged out of the discharge port 546 by the piston 542 will be injected into the patient.

It will also be seen that an inlet check valve 551 may be provided in the inlet port 544 to prevent fluid from being forced from within the piston chamber 541 out through inlet port 544. While the piston 542 is moving toward and returning from the discharge end 552 of chamber 541, it will be seen that the piston 542 covers the inlet port 544 so that liquid will not flow into the piston chamber 541.

Ampule 521 is illustrated as the same as ampule 421 although different configurations can be used. The return movement of the piston 542 in the piston chamber 541 from discharge end 552 to its retracted position creates a partial vacuum between piston 542 and discharge end 552 so that, when the piston 542 uncovers the inlet port 544 in its retracted position, liquid medicament from the ampule 521 having its outlet connected to the inlet port 544 can flow into the piston chamber 541 to be expelled when the piston 442 moves back toward the discharge end 552 of the piston chamber 541.

To drive piston 542 back and forth within piston chamber 541, a driving member 554 such as quartz or the like exhibiting a piezoelectric effect is anchored to housing 540 and connected to piston 542 through an appropriate linkage 555. Because member 554 exhibits a piezoelectric effect, a voltage imposed thereon from controller 536 causes a change of volume of member 554. This change of volume is transmitted to piston 542 via linkage 555 to cause piston 542 to be moved toward the discharge end of chamber 541 to expel the liquid. When the voltage is removed, member 554 moves piston 542 back to its retracted position for chamber 541 to refill from ampule 421. Like the other embodiments of the invention, it will be seen that the movement of the piston 542 toward discharge end 552 can only inject a prescribed volume of fluid so that prevention of overdosage to the patient is insured.

We claim:

1. Fluid dispensing apparatus for injecting fluid into a patient at an average prescribed rate over a prolonged period of time comprising:
   a container defining a fluid chamber therein carrying fluid to be dispensed and an outlet from said fluid chamber connected to the patient;
   a piston slidably mounted in said fluid chamber for forcing fluid from said outlet as said piston is moved toward said outlet;
   an electrical power supply;
   electrically operated driving means for moving said piston toward said outlet when said electrically operated driving means is connected to said power supply; and
   control means for selectively connecting said electrical power supply to and disconnecting said electrical power supply from said electrically operated driving means; said control means including switching means for selectively connecting said electrical power supply to said electrically operated driving means; timing pulse generator means for operating said switching means; programming means for selectively controlling the timing pulse rate output of said timing pulse generator; and mode selector means for selectively activating said programming means to permit adjustment said programming means to change the timing pulse rate output of said timing pulse generator means and for selectively causing said timing pulse generator means to generate the timing pulse rate output selected by said programming means while preventing adjustment of said programming means.

2. The fluid dispensing apparatus of claim 1 wherein said programming means includes encoding means; manually operated input means for selectively encoding said encoding means with the volume of fluid to be injected over a selected time period; manually adjustable time period selector means for selecting the time period over which the fluid is to be injected; and dosage rate logic means operatively connected to said encoding means, said time period selector means, and said timing pulse generator for calculating the required timing pulse output from said timing pulse generator to cause the volume of fluid encoded into said encoding means to be injected within the time period selected in said time period selector means and for causing said timing pulse generator to generate the required timing pulse output.

3. The fluid dispensing apparatus of claim 2 wherein said control means further includes:
   display means for generating a visually perceptive quantified output; and
   monitoring means operatively connected to the timed pulse output of said timing pulse generator for generating an electronic output indicative of the average fluid injection in response to the timed pulse output,
and wherein said mode selector means has a first position connecting said encoding means to said display means to cause said output of said display means to be a quantification of the volume of fluid encoded in said encoding means, activating said manually operated input means to allow the volume of fluid encoded into said encoding means to be changed, and disabling said timing pulse generator to prevent said timing pulse generator from operating said driving means; and having a second position disabling said input means to prevent changing the volume of fluid encoded into said encoding means, enabling said timing pulse generator to operate said driving means, and connecting the electronic output of said monitoring means to said display means to cause the output of said display means to be a quantification of the average fluid injection rate in response to the timed pulse output of said timing pulse generator.

4. The fluid dispensing apparatus of claim 3 wherein said display means includes a liquid crystal display.

* * * * *